US008142408B2

(12) United States Patent
Reddy

(10) Patent No.: US 8,142,408 B2
(45) Date of Patent: Mar. 27, 2012

(54) INSERT CONTAINING A SCROTAL CATCH AND A NON-FLEXIBLE CUP

(76) Inventor: Usha Reddy, Cincinnati, OH (US)

( * ) Notice: Subject to any disclaimer, the term of this patent is extended or adjusted under 35 U.S.C. 154(b) by 236 days.

(21) Appl. No.: 12/488,007

(22) Filed: Jun. 19, 2009

(65) Prior Publication Data

US 2009/0255539 A1 Oct. 15, 2009

Related U.S. Application Data

(62) Division of application No. 11/653,804, filed on Jan. 16, 2007.

(60) Provisional application No. 60/758,876, filed on Jan. 13, 2006, provisional application No. 60/758,877, filed on Jan. 13, 2006, provisional application No. 60/776,434, filed on Feb. 24, 2006.

(51) Int. Cl.
*A61F 13/15* (2006.01)
(52) U.S. Cl. .............................. 604/385.09; 604/385.19
(58) Field of Classification Search ............. 604/385.09, 604/385.19
See application file for complete search history.

(56) References Cited

U.S. PATENT DOCUMENTS

| | | | |
|---|---|---|---|
| 2,842,129 A | 7/1958 | Ernstorff | |
| 3,314,422 A | 4/1967 | Phillips | |
| 3,459,181 A | 8/1969 | Mann | |
| 3,517,666 A | 6/1970 | Atlee | |
| 3,616,798 A | 11/1971 | Garfinkel | |
| 4,155,360 A | 5/1979 | Erickson | |
| 4,590,931 A | 5/1986 | Kidwell, Jr. | |
| 4,644,945 A | 2/1987 | Thorner | |
| 4,675,012 A | 6/1987 | Rooyakkers | |
| 4,731,063 A | 3/1988 | Newkirk | |
| 4,759,355 A | 7/1988 | Thrower | |
| 4,892,536 A | 1/1990 | DesMarais et al. | |
| 4,946,454 A | 8/1990 | Schmidt | |
| 5,486,168 A | 1/1996 | Runeman et al. | |
| 5,514,121 A * | 5/1996 | Roe et al. | 604/385.19 |
| 5,547,466 A | 8/1996 | McRoberts et al. | |
| 5,556,393 A | 9/1996 | Ronnberg | |
| 5,558,659 A | 9/1996 | Sherrod et al. | |
| 5,651,778 A | 7/1997 | Melius et al. | |
| 5,702,381 A | 12/1997 | Cottenden | |
| 5,716,350 A | 2/1998 | Ryan | |
| 5,718,003 A | 2/1998 | Gwinn | |
| 5,810,799 A | 9/1998 | Slater | |
| 6,132,412 A | 10/2000 | Jones | |
| 6,245,036 B1 | 6/2001 | McRoberts et al. | |
| 6,375,643 B1 | 4/2002 | Moorhead et al. | |
| 6,562,015 B1 | 5/2003 | Wilson | |
| 6,817,992 B1 * | 11/2004 | Sassak et al. | 604/385.09 |
| 6,979,325 B2 | 12/2005 | Reddy | |
| 7,178,174 B2 | 2/2007 | Soderstrom | |
| 7,276,054 B2 * | 10/2007 | Mishima et al. | 604/385.01 |

(Continued)

FOREIGN PATENT DOCUMENTS

EP 0573521 4/1997

(Continued)

*Primary Examiner* — Lynne Anderson
(74) *Attorney, Agent, or Firm* — Dinamore & Shohl LLP

(57) ABSTRACT

An insert containing a scrotal catch and a non-flexible cup, wherein the scrotal catch is configured to support, protect or cover at least a portion of a male's scrotum and the non-flexible cup is configured to support, protect or cover at least a portion of a male's genitalia, is provided.

20 Claims, 6 Drawing Sheets

U.S. PATENT DOCUMENTS

| | | |
|---|---|---|
| 7,553,300 B2 | 6/2009 | Elfstrom et al. |
| 2003/0028161 A1* | 2/2003 | Carballo .................. 604/349 |
| 2003/0125690 A1 | 7/2003 | Hermansson et al. |
| 2004/0049835 A1 | 3/2004 | Horikoshi et al. |
| 2004/0092851 A1 | 5/2004 | Littell |
| 2004/0097893 A1 | 5/2004 | Elfstrom et al. |
| 2004/0111073 A1 | 6/2004 | Hermansson et al. |
| 2005/0192551 A1 | 9/2005 | Reddy |
| 2007/0078420 A1 | 4/2007 | Sugiyama et al. |
| 2007/0163030 A1 | 7/2007 | Reddy |
| 2008/0082072 A1 | 4/2008 | Helmfridsson et al. |

FOREIGN PATENT DOCUMENTS

| | | |
|---|---|---|
| WO | WO9848753 A1 | 11/1998 |
| WO | WO 2006016240 A1 * | 2/2006 |

* cited by examiner

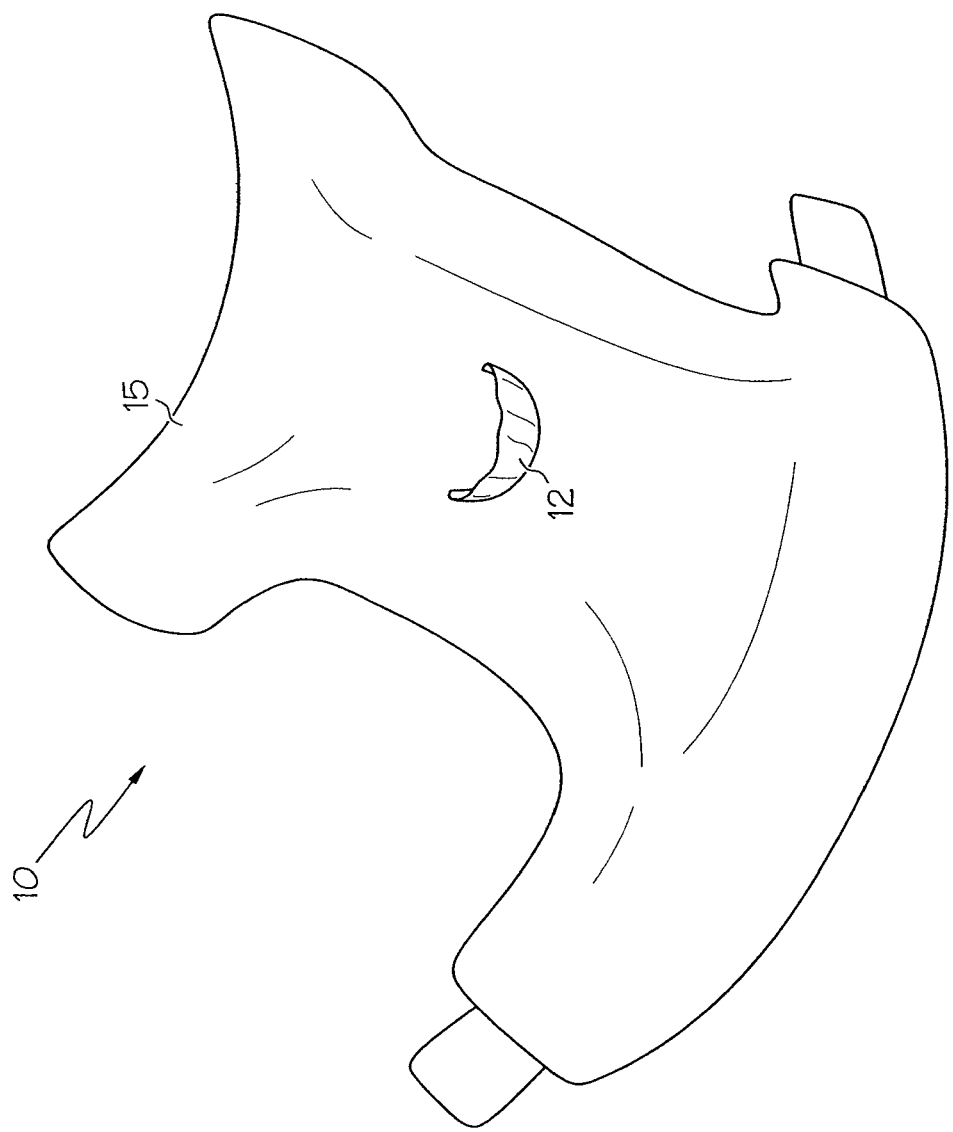

INSERT CONTAINING A SCROTAL CATCH AND A NON-FLEXIBLE CUP

RELATED APPLICATIONS

This application is a divisional of pending application Ser. No. 11/653,804, filed Jan. 16, 2007, and claims priority under 35 U.S.C. §119 of U.S. Provisional Application Ser. Nos. 60/758,876 filed Jan. 13, 2006, 60/758,877 filed Jan. 13, 2006 and 60/776,434 filed Feb. 24, 2006.

FIELD OF THE INVENTION

The present invention is directed to garments, articles and inserts comprising a scrotal catch.

BACKGROUND OF THE INVENTION

A man's genital area is a difficult area to support, cover, and/or protect due to its heightened sensitivity, location on the body, and general shape. This is especially true following surgery of the male genitalia, the inferior abdomen, and/or of the pelvis. Because the male genital area is the site of waste expulsion, it is difficult to keep these surgical areas clean and prevent contamination from fecal matter, urine, and associated pathogens until the surgical site has healed. The inability to keep these wound sites clean can result in wound infections, inflammation, and additional scarring which, in turn, can lead to the need for more surgery. Accordingly, there is a need for an article that keeps surgical areas clean.

In addition, it is also harmful for waste material to remain in prolonged contact with the male genitalia. This is a very common problem because there are no barriers preventing the migration of fecal matter to the genital area within an absorbent article. This migration of fecal matter onto the male genitalia makes it very difficult and time consuming for caregivers to effectively clean the soiled areas and if fecal matter remains in prolonged contact with the male genitalia it can contribute to urinary tract infections, inflammation of the male genitalia and/or meatal stenosis. These painful conditions of the male genitalia have been shown to delay toilet training or actually cause regression of a child who has been previously toilet trained. Accordingly, there is a need to prevent the contamination of the male genitalia with fecal matter in an absorbent article.

SUMMARY OF THE INVENTION

Embodiments of the present invention are directed to garments comprising a scrotal catch, wherein the scrotal catch is attached to at least a portion of the garment, and wherein the scrotal catch is configured to support, protect and/or cover at least a portion of a male's scrotum.

Embodiments of the present invention are also directed to inserts comprising a scrotal catch and a non-flexible cup, wherein the scrotal catch is configured to support, protect and/or cover at least a portion of a male's scrotum and the cup is configured to support, protect and/or cover at least a portion of a male's genitalia.

Embodiments of the present invention are further directed to absorbent articles comprising a top sheet, a bottom sheet, an absorbent core disposed between the top sheet and the bottom sheet, and a scrotal catch attached to at least a portion of the top sheet, wherein the scrotal catch is configured to support, protect and/or cover at least a portion of a male's scrotum.

BRIEF DESCRIPTION OF THE DRAWINGS

The following detailed description will be more fully understood in view of the drawings in which:

FIG. 7 is a top view depicting a scrotal catch in one embodiment of the present invention.

Figure 1:
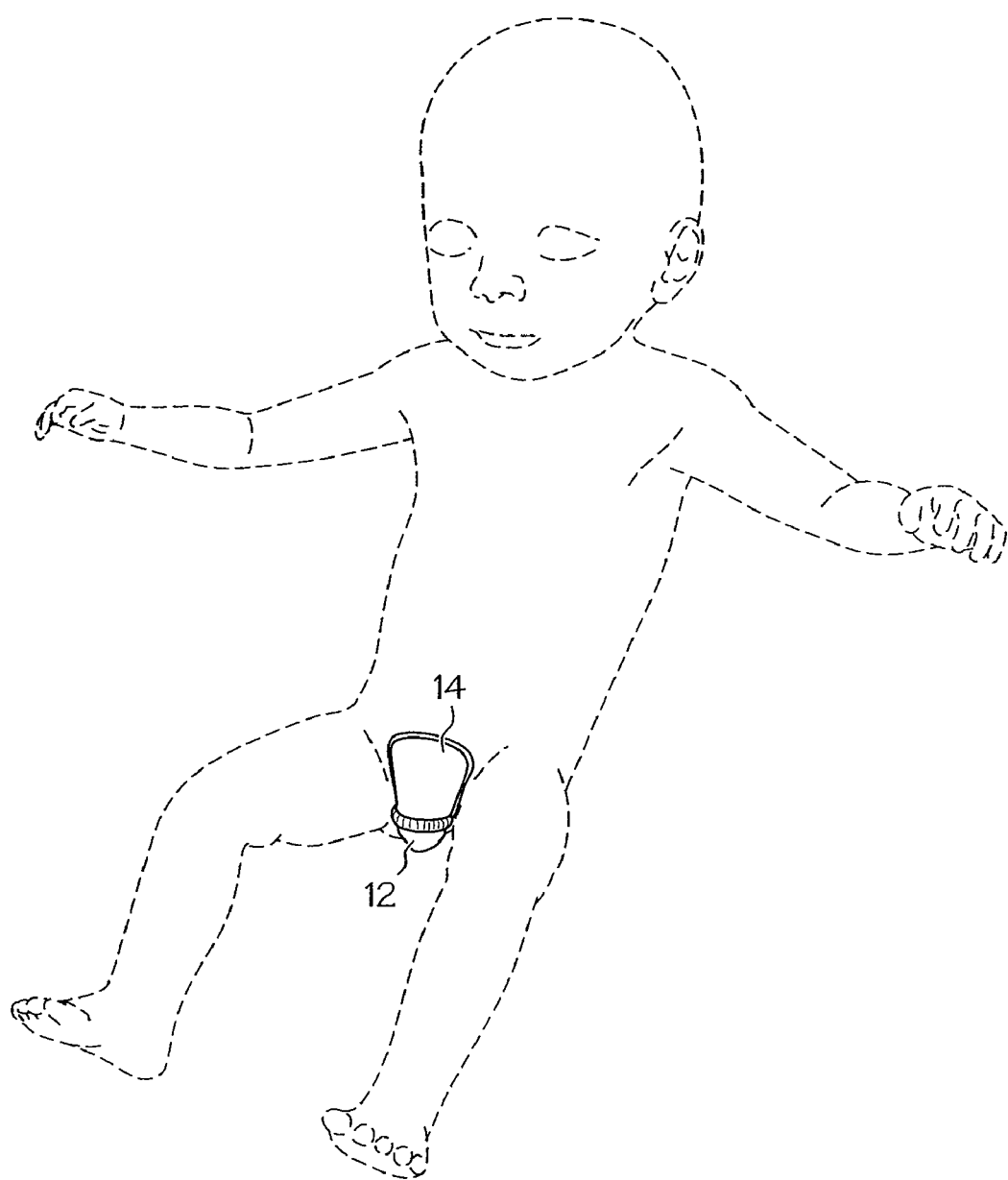
FIG. 1 is a front view showing a baby that has been fitted with one embodiment of the present invention.

The embodiments set forth in the drawings are illustrative in nature and are not intended to be limiting of the invention defined by the claims. Moreover, individual features of the drawings and the invention will be more fully apparent and understood in view of the detailed description.

DETAILED DESCRIPTION OF EMBODIMENTS

Within the context of this specification, each term or phrase below will include the following meaning or meanings.

"Absorbent article" refers to garments that absorb and contain exudates, and more specifically, refers to garments that are placed against or in proximity to the body of a wearer to absorb and contain the various exudates discharged from the body. A non-exhaustive list of examples of absorbent articles includes diapers, diaper covers, cloth diapers, disposable diapers, training pants, and adult incontinence products. This term includes both disposable and non-disposable absorbent articles.

"Attached" refers to the joining, adhering, bonding, connecting, or the like, of at least-two elements. Two elements will be considered to be attached together when they are attached directly to one another or indirectly to one another, such as when each is bonded to intermediate elements. The two elements can be attached in any suitable manner that permits or allows them to perform the intended or described function.

"Breathable" refers to a material present in one or more layers that permits vapors to travel through the material while still preventing exudates from passing through the material. Exemplary breathable materials may include woven webs, nonwoven webs, composite materials such as film-coated nonwoven webs, and microporous films. Furthermore, the films may be apertured.

"Cup" refers to a non-flexible enclosure configured to support, protect and/or cover at least a portion of a male's genitalia.

"Disposable" refers to articles, which are designed to be discarded after a limited use, rather than being laundered or otherwise restored for reuse.

"Enclosure" means to substantially cover by encasing, surrounding or fitting over or around at least a portion of the body.

"Fabric" refers to wovens, scrims, knits, nonwoven webs and other like materials.

"Film" refers to a material present in one or more layers made using a film extrusion process, such as a cast film or blown film extrusion process. The term includes apertured films, slit films, and other porous films, which constitute liquid transfer films, as well as films, which do not transfer liquid. The term also includes elastic films, inelastic films and combinations of such films.

"Flexible" refers to a material present in one or more layers which is compliant and which will readily conform to the general shape and contours of an object.

"Garment" refers to any type of product, which may be worn. Examples include, but are not limited to, diapers, training pants, medical garments, swim pants, absorbent articles, undergarments, clothing, pants, shorts, medical dressings, supports, incontinence products and the like.

"Layer" when used in the singular can have the dual meaning of a single element or a plurality of elements.

"Liquid impermeable" refers to a material present in one or more layers through which liquid, such as urine, will not pass.

"Liquid permeable material" refers to a material present in one or more layers, such as a film, nonwoven fabric, woven fabric, scrim or open-celled foam, which is porous, and which is water pervious due to the flow of water and other aqueous liquids through the pores. The pores in the film or foam, or spaces between fibers or filaments in woven or nonwoven fabrics, are large enough and frequent enough to permit leakage and flow of liquid water through the material.

"Multilayer Laminate" means a laminate having multiple layers, which are of the same or different constructions. For example, the laminate can include a combination of spunbond and meltblown layers, such as a spunbond/meltblown/spunbond (SMS) laminate, a combination of film and nonwoven layers or a combination of film layers. In addition, a multilayer film may be laminated to one or more nonwoven webs, using conventional adhesive bonding or thermal bonding techniques known in the art.

"Non-flexible" refers to a material present in one or more layers, which will not readily conform to the general shape and contours of an object. This term includes, but is not limited to, rigid materials, semi-rigid materials, soft-pliable materials with structural elements to maintain a non-flexible form, and combinations thereof.

"Nonwoven" refers to materials and webs of material present in one or more layers having a structure of individual fibers or filaments that are interlaid, but not in an identifiable manner as in a knitted fabric. Nonwoven fabrics or webs may be formed from many processes such as, meltblowing processes, spunbonding processes, air laying processes, and bonded carded web processes.

"Porous" refers to a material present in one or more layers that is able to pass or transport a measurable amount of liquid under conditions normally encountered in the use of the material. The material may be rendered porous by puncturing or aperturing, or rendered porous by mixing a polymer with filler, forming a film from the mixture, and stretching the film.

"Removably attached" refers to two elements being connected or connectable such that the elements tend to remain connected absent a separation force applied to one or both of the elements, and the elements being capable of separation without substantial permanent deformation or rupture. The required separation force is typically beyond that encountered while wearing the article.

"Scrotal Catch" refers to an enclosure present in one or more layers configured to support, protect and/or cover at least a portion of a male's scrotum.

These terms may be further defined with additional language in the remaining portions of the specification.

The present invention is directed to a scrotal catch which is configured to support, protect and/or cover at least a portion of a male's scrotum. The principles of the present invention can be incorporated into any suitable garment, device or absorbent article in which there is desire to support, protect and/or cover at least a portion of a male's scrotum. Examples of suitable disposable and non-disposable garments in which the scrotal catch may be attached include, but are not limited to, diapers, training pants, incontinence products, swim wear, other personal care or health care garments, swim pants, athletic clothing, pants and shorts, and the like. Examples of suitable uses for the scrotal catch include, but are not limited to, wound protection, athletic support and/or protection, wound covering, protection from infection, protection from wetness, protection from fecal matter, compartmentalization of a garment, or combinations thereof. In addition, the principles of the present invention may be employed for a male of any age.

For ease of discussion, the following detailed description will be made in the context of an absorbent article, which is adapted to be worn by infant, baby or toddler males. However, it will be appreciated that the invention encompasses other embodiments for other uses, a few examples of which are given above. Additionally, the invention will be described in the context of its various configurations, however it should be appreciated that alternative arrangements of the invention can comprise any combination of such configurations.

Figure 4:
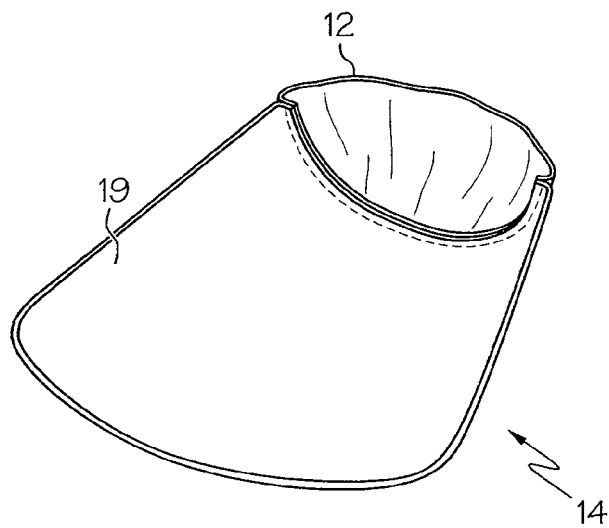
FIG. 4 is a back view depicting a scrotal catch in one embodiment of the present invention.
Figure 5:
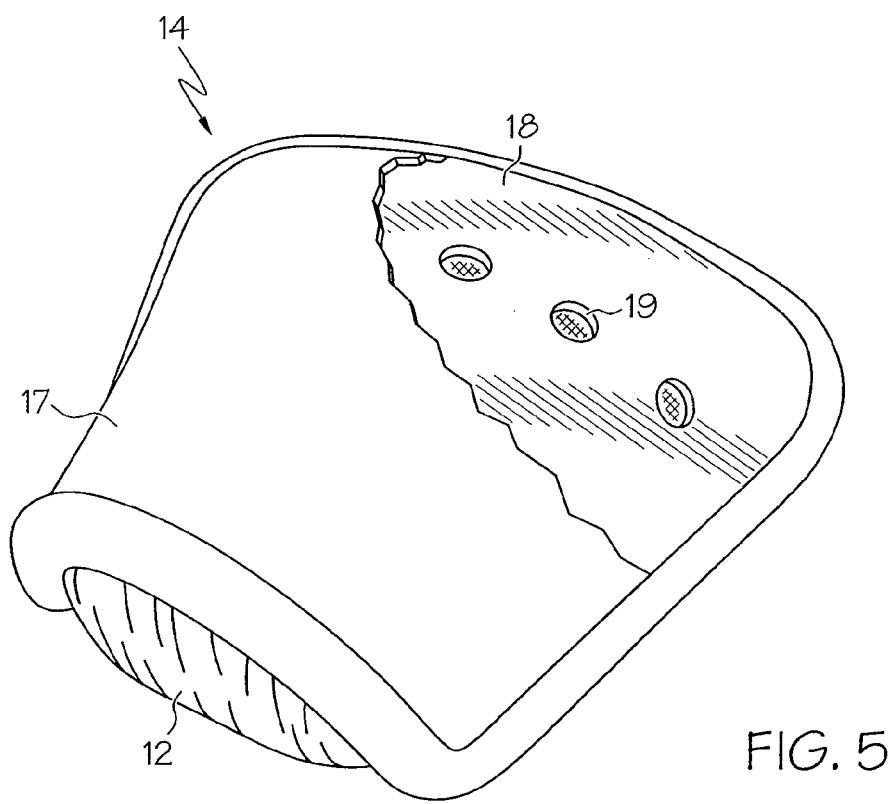
FIG. 5 is an angled front view depicting a scrotal catch in another embodiment of the present invention.
Figure 6:
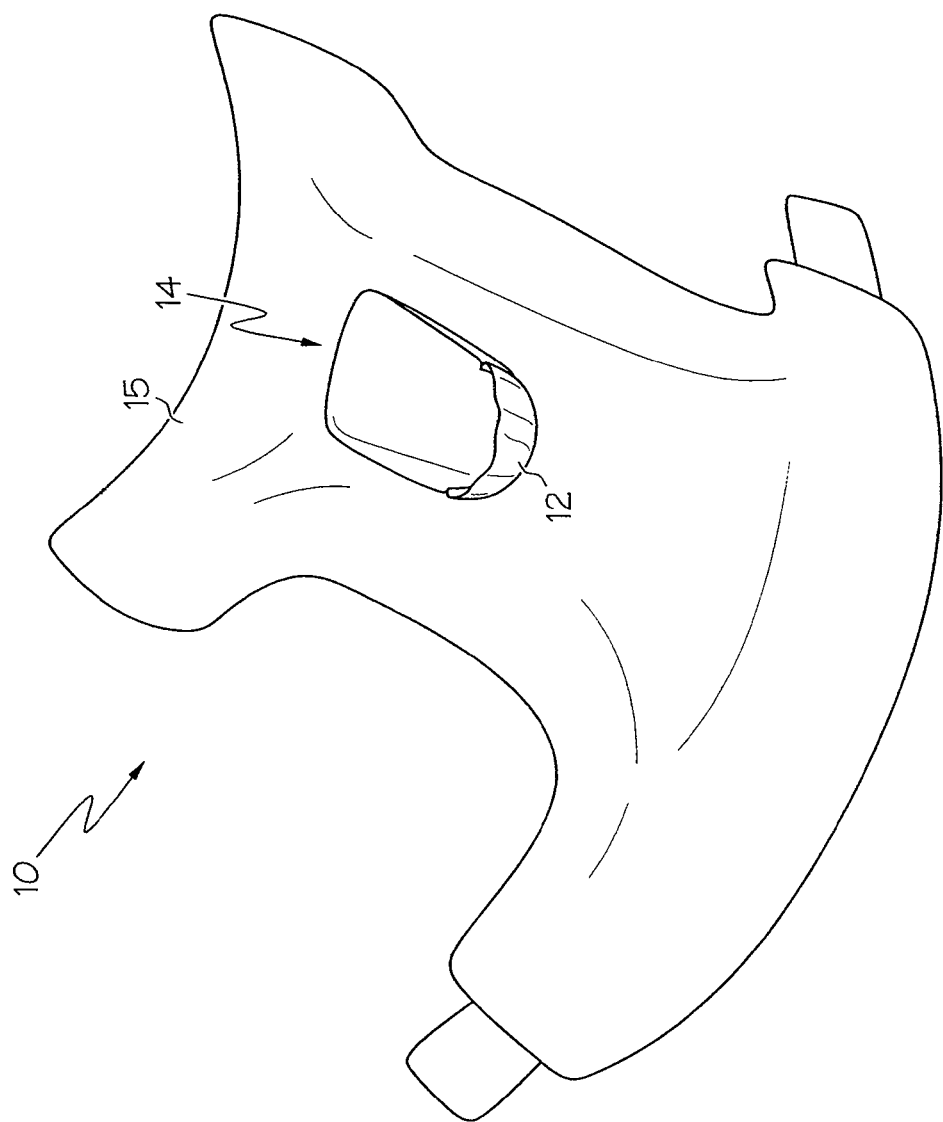
FIG. 6 is a top view depicting a scrotal catch in another embodiment of the present invention.

Embodiments of the scrotal catch are illustrated in FIGS. 1-7. As illustrated in FIGS. 6-7, an absorbent article 10 comprises a scrotal catch 12 which is attached to at least a portion of the absorbent article 10, wherein the scrotal catch 12 is configured to support, protect and/or cover at least a portion of a male's scrotum. The scrotal catch is configured to be an enclosure of a male's scrotum. If desired, the scrotal catch may also or alternatively be configured to provide a barrier to reduce and/or prevent fecal matter from contacting the male's genital area. In certain embodiments, the scrotal catch allows for the separation of the interior surface of the absorbent article into anterior and posterior compartments. This compartmentalization of the absorbent article reduces and/or prevents the fecal matter from entering the anterior compartment containing the male's genitalia by retaining the fecal matter in the posterior compartment of the absorbent article.

It will be appreciated that various materials may be employed for the scrotal catch of the present invention. Examples of suitable materials include one or more layers of a nonwoven fabric, a woven fabric, a scrim, film, an open-celled foam or any combinations thereof. In addition, it will be appreciated that the one or more layers of the material may display various properties. For example, one or more layers of the scrotal catch may be breathable, liquid permeable, liquid impermeable, flexible, non-flexible or any combination thereof.

It will also be appreciated that there are various configurations for an absorbent article to which the scrotal catch may be attached, any of which may be employed herein. In one embodiment, the absorbent article comprises a top sheet, a bottom sheet, an absorbent core disposed between the top sheet and the bottom sheet, and a scrotal catch attached to at least a portion of the top sheet. The terms "top sheet" and "bottom sheet" denote the relationship of these materials or layers with respect to the absorbent core. It is appreciated that the term "top sheet" refers to the sheet which is adjacent to the skin of the user of the absorbent article while the term "back sheet" refers to the sheet which is not adjacent to skin of the user of the absorbent article. It is appreciated and understood that additional layers may be present between the absorbent core and the top sheet and/or bottom sheet, and that additional layers and other materials may be present on the side opposite the absorbent core from either the top sheet or the bottom sheet. It is further appreciated that the one ore more layers of the absorbent core may comprise similar or different breathability, liquid permeability and flexibility properties. For example, in one embodiment, the absorbent article comprises a liquid impermeable, breathable back sheet, an absorbent core and a liquid permeable, breathable top sheet.

The scrotal catch is attached to the absorbent article. In certain embodiments, the scrotal catch may be removably attached to the absorbent article. One skilled in the art will appreciate the various means in which the scrotal catch may be removably attached to the absorbent article, any of which may be employed herein. Examples include, but are not limited to, adhesives, tackifiers, snaps, buttons, hook materials, ties, straps and any combination thereof.

Figure 2:
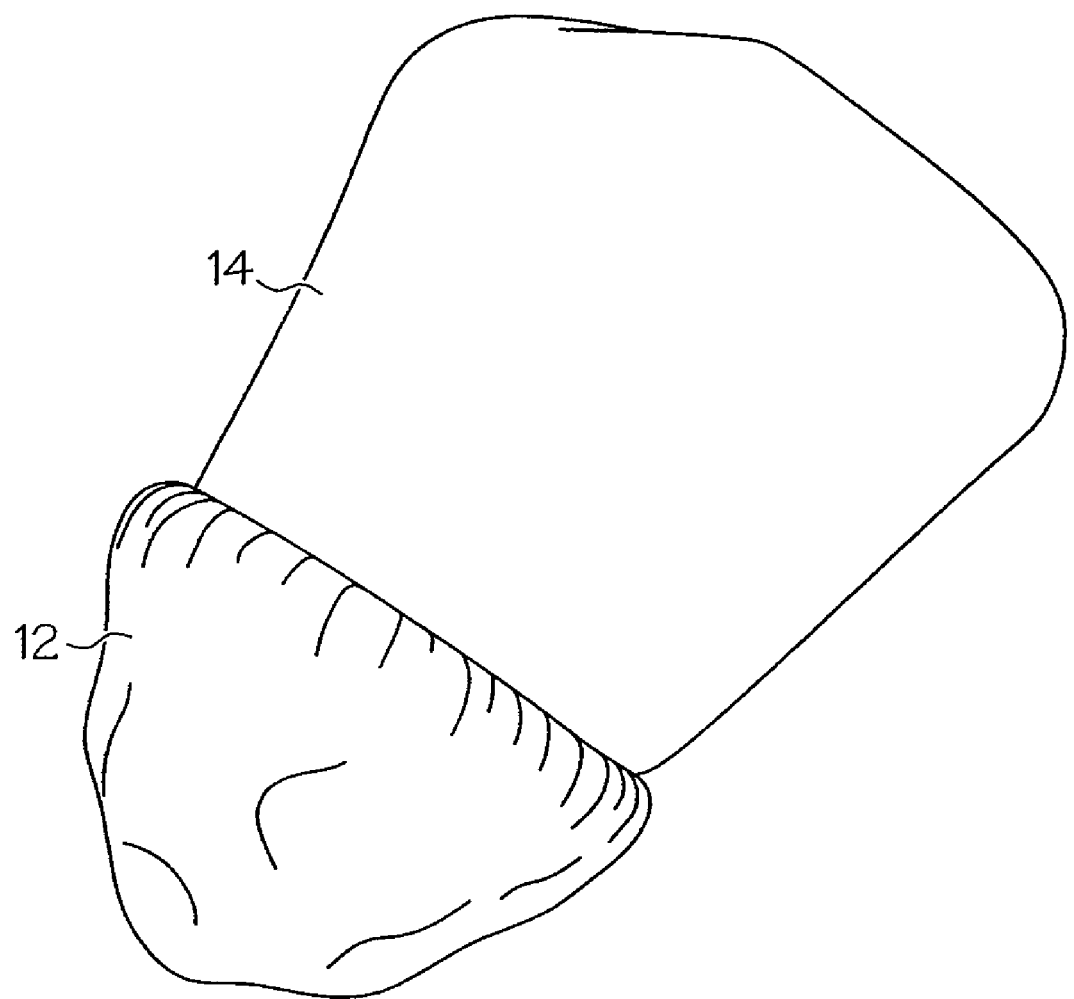
FIG. 2 is an angled front view depicting a scrotal catch in one embodiment of the present invention.
Figure 3:
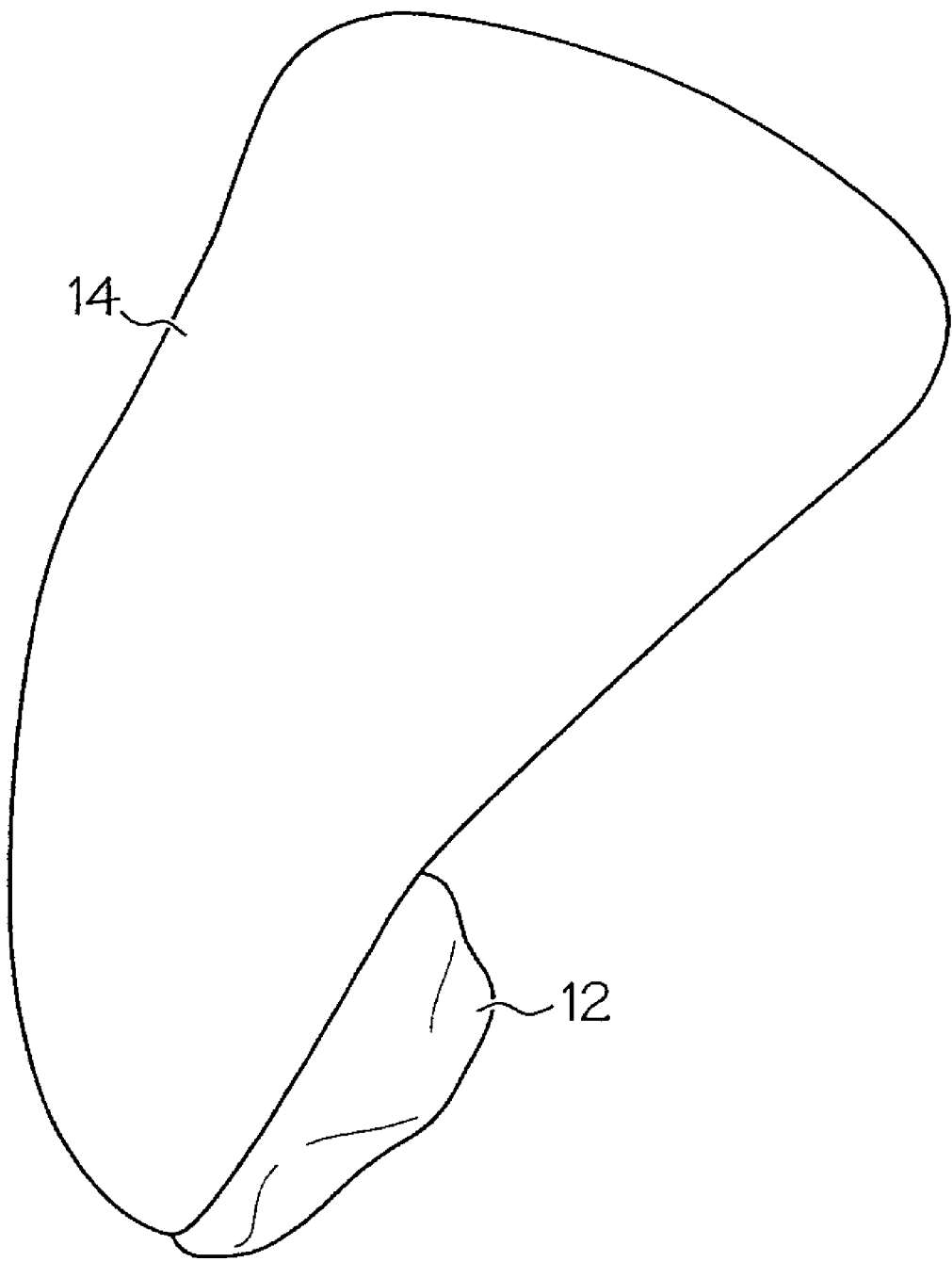
FIG. 3 is an angled side view depicting a scrotal catch in another embodiment of the present invention.

As shown in FIG. 6, the absorbent article 10 may further comprise a non-flexible cup 14. While the scrotal catch is configured to support, protect and/or cover at least a portion of a male's scrotum, the non-flexible cup is configured to support, protect and/or cover at least a portion of a male's genitalia. In certain embodiments, as depicted in FIG. 3, the cup 14 is configured to support, protect and/or cover all of a male's genitalia. In other embodiments, as depicted in FIGS. 1-2, the cup 14 is configured to support, protect and/or cover a male's penis. The addition of the non-flexible cup to the absorbent article not only assists in the reduction and/or prevention of fecal matter from contacting a male's genital area, but also or alternatively may serve to protect the genital area from external pressure.

It will be appreciated and understood that various configurations, shapes and sizes may be employed for the non-flexible cup of the present invention. It will also be appreciated that the non-flexible cup may be attached to various portions of the absorbent article comprising a scrotal catch and such attachment may be permanent or removable. In certain embodiments, the non-flexible cup is attached to at least a portion of the top sheet. In other embodiments, the non-flexible cup is attached to at least a portion of the scrotal catch. In further embodiments, the non-flexible cup is attached to at least a portion of the scrotal catch and the top sheet. In further embodiments, the absorbent article is configured so that the non-flexible cup is provided between the top sheet and the absorbent core.

As shown in FIGS. 1-5, the scrotal catch 12 may be attached to various portions of the non-flexible cup 14. As depicted in FIGS. 1-2, the scrotal catch 12 is attached to the exterior surface of the non-flexible cup 14. As depicted in FIGS. 3-5, the scrotal catch 12 is attached to the exterior surface of the non-flexible cup 14. It is also appreciated that the scrotal catch may be attached to the exterior and interior surface of the non-flexible cup.

It will be appreciated that various materials may be employed for use with the non-flexible cup of the present invention. Examples of suitable materials include one or more layers of a nonwoven fabric, a woven fabric, a scrim, film, an open-celled foam, plastic or any combinations thereof. In addition, it will be appreciated the various properties in which the one or more layers of the material may comprise. For example, one or more layers of the non-flexible cup may be breathable, liquid permeable or liquid impermeable. As depicted in FIG. 5, the non-flexible cup 14 comprises a breathable, liquid permeable bottom layer 19, middle layer 18 and top layer 17. In one embodiment, the middle layer 18 comprises a plastic material. However it should be appreciated that alternative arrangements of the non-flexible cup may be employed, which includes additional layers and other materials on the surface and sides of the non-flexible cup.

In certain embodiments, the absorbent article may be configured to provide an opening in the top sheet and/or the absorbent core for receiving the non-flexible cup or for receiving at least a portion of a male's genitalia when the non-flexible cup is not included in the absorbent article.

The absorbent article may also comprise a moisture-indicating device. The remote moisture indicators are designed to allow an individual or a caregiver of an individual to be alerted when moisture is present in an absorbent article without the need to remove the clothing. By allowing the caregiver or the individual to be alerted about a wet garment, it can be changed in an appropriate timeframe, reducing the time of contact with a soiled garment. By preventing prolonged contact with either urine or fecal matter, the general health and hygiene of the skin is improved, which reduces the risk of, for example, diaper rash, skin breakdown, bed-sores, and urinary tract infections.

It will be appreciated that various moisture indicating devices may be employed in the present invention. In one embodiment, the moisture indicating device comprises a sensor, a neck with a first end and a second end, and a moisture indicator, wherein the sensor is attached to the first end of the neck and the moisture indicator is attached to the second end of the neck. It will be appreciated that the sensor may be placed anywhere within the absorbent article to facilitate the detection of moisture. In one embodiment, the sensor is placed in the genital area of the absorbent article. It will also be appreciated the various means in which the information obtained from the sensor will transfer to the moisture indicator. In one embodiment, the information is transferred by physical means, such as with capillary action. In another embodiment, the information is transferred by electrical means. It will also be appreciated that the moisture indicator may be placed anywhere desirable outside of the absorbent article for easy access, viewing or readout. Furthermore, one skilled in the art will appreciate the various means in which the moisture in the absorbent article may be indicated. For example, the moisture indicator may be visual, such as with a color change by chemical means or electrical means, tactile, such as vibrations indicating a wet diaper, or aural, such as an audible alarm.

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. An insert comprising a scrotal catch and a non-flexible cup, wherein the scrotal catch is liquid permeable and flexible, such that the scrotal catch conforms to a contour of a scrotum, and wherein the scrotal catch is configured to support, protect or cover at least a portion of the scrotum and to provide a barrier to reduce or prevent the passage of fecal matter to a genital area, and wherein the cup is configured to support, protect or cover at least a portion of a male's genitalia.

2. The insert of claim 1, wherein the cup is configured to support, protect or cover a male's penis.

3. The insert of claim 1, wherein the scrotal catch is removably attached to the cup.

4. The insert of claim 1, wherein the scrotal catch is removably attached to an interior of the cup, an exterior of the cup, a bottom of the cup, or a combination thereof.

5. The insert of claim 1, wherein the scrotal catch is comprised of a material selected from the group consisting of a woven fabric, a non-woven fabric, a film, and any combination thereof.

6. The insert of claim 1, wherein the scrotal catch comprises a breathable material.

7. The insert of claim 1, wherein the cup is porous.

8. The insert of claim 1, wherein at least a portion of the cup is covered with a material selected from the group consisting of a woven fabric, a non-woven fabric, a film, and any combination thereof.

9. The insert of claim 8, wherein the material is breathable.

10. The insert of claim 9, wherein the cup is configured to provide a barrier to reduce or prevent the passage of fecal matter to the genital area and is configured to protect the genital area from external pressure.

11. The insert of claim 1, wherein the scrotal catch is attached to at least a portion of a garment.

12. The insert of claim 11, wherein the garment comprises a diaper, an absorbent article, an undergarment, a piece of clothing, a dressing, a support, an incontinence garment or a combination thereof.

13. The insert of claim 1, wherein the cup is attached to at least a portion of a garment.

14. The insert of claim 13, wherein the garment comprises a diaper, an absorbent article, an undergarment, a piece of clothing, a dressing, a support, an incontinence garment or a combination thereof.

15. The insert of claim 14, wherein the scrotal catch is attached to at least a portion of the garment.

16. The insert of claim 13, wherein the garment is an absorbent article comprising a top sheet, a bottom sheet, and an absorbent core disposed between the top sheet and the bottom sheet.

17. The insert of claim 16, wherein an opening is provided in the top sheet and/or absorbent core for receiving the cup.

18. The insert of claim 16, wherein the cup is attached to at least a portion of the top sheet.

19. The insert of claim 16, wherein the cup is disposed between the top sheet and the absorbent core.

20. The insert of claim 18, wherein the top sheet further comprises a sleeve, wherein the sleeve is configured to receive the cup.

* * * * *